United States Patent [19]

McDevitt

[11] 4,112,770
[45] Sep. 12, 1978

[54] MOLTEN METAL SAMPLER

[76] Inventor: Robert F. McDevitt, Box 551 Ogden Dunes, Ogden Dunes, Ind. 46368

[21] Appl. No.: 792,394

[22] Filed: Apr. 29, 1977

Related U.S. Application Data

[60] Division of Ser. No. 720,697, Sep. 7, 1976, which is a continuation of Ser. No. 565,396, Apr. 4, 1975, abandoned.

[51] Int. Cl.² .............................................. G01N 1/12
[52] U.S. Cl. ............................................. 73/425.4 R
[58] Field of Search ................ 73/425.4 R, DIG. 9; 164/4

[56] References Cited

U.S. PATENT DOCUMENTS

| | | | |
|---|---|---|---|
| 3,457,790 | 7/1969 | Hacket | 73/425.4 |
| 3,552,214 | 1/1975 | Collins | 73/425.4 |
| 3,646,816 | 3/1972 | Hance et al. | 73/425.4 |
| 3,859,857 | 1/1975 | Falk | 73/425.4 |
| 3,897,689 | 8/1975 | Boron | 73/425.4 R |

FOREIGN PATENT DOCUMENTS 745,778 2/1933 France ........................ 249/52

*Primary Examiner*—S. Clement Swisher

[57] ABSTRACT

Molten metal sampling devices and methods form samples of solid metal, which have been formed in a mold. The resulting sample consists of plurality of parts of various sizes and shapes convenient for analysis. The parts are connected by thinner elements permitting ready separation.

27 Claims, 10 Drawing Figures

MOLTEN METAL SAMPLER

The subject application is a division of my patent application Ser. No. 720,697 filed Sept. 7, 1976, a continuation of Ser. No. 565,396 filed Apr. 14, 1975, now abandoned.

More particularly, the purpose of the invention is to provide a safe and simple method whereby a cast sample for example, may be obtained from a flowing metal stream when molten metal is being transferred by pouring from one type vessel to another. The case sample may consist of a disc with one or more smaller cast extensions attached to the disc. The size and shape of the casting is designed to provide a precision sample, requiring a minimum of preparation, that meets laboratory testing procedures. The disc may be used directly for spectrographic analysis or can be drilled to provide a sample for wet chemical analysis. In addition, the sample may be sawed and polished for use in metallographic study of grain structure, cleanliness, etc. The smaller cast extensions are of precision dimensions with indexed separation points to permit detaching a sample of precise weight, minimizing preparation. These smaller samples are suited for analysis of such elements as sulfur or carbon.

The entire sample (disc and extension) can be cast in a two piece mold assembly made of a material with optimum cooling venting and dimensional characteristics. This sample is representative of the material being tested and can be used for either chemical analysis or metallographic examinations.

DESCRIPTION OF THE TESTING PROCEDURE

In the processing of metals in the molten state it is necessary to obtain a sample representative of the present material, at various stages in the processing, for the evaluation of either its chemical composition or metallographic structure.

The device or sampler embodying the subject invention is preferably designed to obtain a quick chilled sample from the flowing metal as it is transferred by pouring from one type vessel to another. It is primarily designed to be used where molten steel is poured from a teeming ladle into a mold. The molten steel is teemed through a nozzle in the bottom of the ladle, and the resulting stream is controlled through use of a mechanical, electro, or hydraulic valve arrangement. The diameter of the stream can be from ¾ inch to 3½ inches depending on the rate of flow desired.

The device also has application in the continuous casting process during transfer of molten metal from ladle to tundish to mold under controlled condition. This device has further application in any area or with any molten metal where the molten metal is transferred from one vessel to another under controlled conditions.

For many years the typical method of sampling molten metal in the steel industry was to use what was defined as a spoon. The spoon consisted of a deep bowl type ladle or sampler attached to the end of a long handle and made of either cast or forged steel. The spoon varied in size and had a lip to facilitate pouring. In practice the pouring stream was controlled to a slow or partial stream and the spoon was then dipped into the stream of metal to obtain the sample. The spoon was usually dipped into either the right or left side of the stream, whichever was most convenient, and partially filled with molten metal. The molten metal content of the spoon was then poured into a small test mold positioned on the platform. The casting from this mold provided a sample 4 inches to 8 inches long, tapered, and 1 inches to 2 inches square in cross-section. The sample could be sawed or drilled in the laboratory to provide samples for wet chemistry analysis, spectrographic analysis or metallographic evaluations. The samples obtained as described above are used to represent a portion of the metal in the teeming ladle at given intervals in the pouring process.

This conventional method of sampling is not only wasteful from the standpoint of time and material but also exposes the molten metal to atmospheric oxygen which can cause variations in the chemical content of the sample. The degree of the chemical variation is dependent on the grade of steel as well as the techniques of the individual doing the sampling. The effect is most pronounced with the elements of carbon and manganese with varying effects on other elements. Although the steel industry has been aware of the phenomenon and does make corrections; much could be gained by minimizing this condition. Other disadvantages of this conventional method are the need to arrest the stream and the extreme safety hazards involved with taking a sample when the molten metal stream cannot be controlled.

Advantages of the invention or inventions over the spoon technique are:
1. Minimum exposure of the sample to atmospheric oxygen.
2. Simplified sampling technique eliminating the heavy spoon and repouring technique.
3. Elimination of the need to arrest the molten metal stream flow.
4. Precision cast samples with a quick chill and tailored for minimum preparation.
5. Representative and reproducible results at a minimum of expense.
6. Safe procedure in obtaining samples.

In view of the foregoing, one of the important objects of the invention is to provide an elongated device for obtaining a sample of a liquid, such as molten metal, which comprises, among other things, a pair of half sections forming a chamber, tubular means which has an inner extremity communicatively connected to the chamber and an outer extremity provided with an entrance for initially receiving molten metal for flow into the chamber, means at one extremity of the device for holding the sections together, and means at its opposite extremity for holding the sections and tubular means assembled, and wherein one or both of these holding means may serve to facilitate disassembly of the sections. More particularly in this respect, one of the holding means for the sections comprises clip means, and an appendage held in place by this clip means may be utilized for identificating purposes and effect release of the clip means, and the means for holding the sections and tubular means may be operated to facilitate disassembly of these components.

A significant object of the invention is to provide a device of the character described above in which each section includes a relatively large head portion provided with a recess and an extended portion having a center groove therein so that when the sections are correctly assembled the recesses will form a primary chamber and the grooved extensions will form a tubular formation communicating with the chamber, and the extensions are provided with additional grooves forming secondary chambers for receiving samples of molten metal from the primary chamber.

Also, an object of the invention is to provide a device as described in the preceding paragraph in which the head portions of the sections are also provided with recesses which form additional secondary chambers which receive molten metal from the primary chamber.

Also, an object is to provide a device whereby different forms of sample portions may be obtained. More particularly, one sample may include a large head or stem, and longitudinal and offset portions joined to the head.

Additional objects and advantages of the invention reside in providing a device which is safe and efficient to use, durable and comprised of components which can be economically manufactured and assembled on a production basis.

Other objects and advantages will become apparent after the description hereinafter set forth is considered in conjunction with the drawings annexed hereto.

The claims in the subject application are primarily directed to FIGS. 7, 8, 9 and 10, view of FIGS. 1 through 6 of the drawings.

Figure 1:
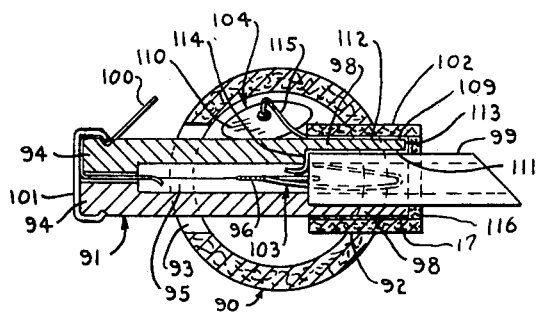
FIG. 1 is a sectional view of a connector and a device operatively connected thereto.

FIG. 1 discloses a modified form of a connector generally designated 90 and a modified device generally designated 91. The connector is provided with a pair of aligned round side openings 92 and 93 of different diameters disposed on a line transverse to the longitudinal axis of the connector.

The device 91 is quite similar to the device shown in FIG. 12 of said parent application, and comprises a pair of recessed half sections 94 constructed to provide a chamber 95 and side vents 96. These half sections also include channel portions 98 which form a tubular formation for receiving an inner extremity of a tubular means 99. The device also includes an appendage 100, clip means 101, and a sleeve 102, like those described above including a metal deoxidizing element generally designated 103 and what may be termed a trigger assembly generally designated 104.

Figure 4:
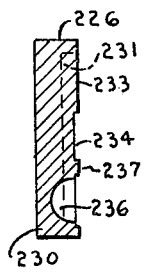
FIG. 4 is a transverse section taken substantially on line 4—4 of FIG. 2.
Figure 5:
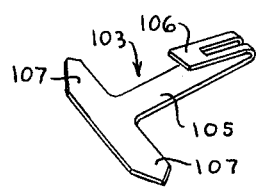
FIG. 5 is a perspective view of a deoxidizing element which may be utilized on conjunction with the device shown in FIG. 2.
Figure 6:
FIG. 6 is a perspective view of a modified form of a deoxidizing element which may be utilized in a mode different from that of the element shown in FIG. 5.

The deoxidizing element 103 may be designed and constructed as desired but is preferably generally T-shaped or articulated as exemplified in FIG. 5 and includes a stem 105 having a slotted continuation 106 bent back at an acute angle over the stem and a pair of opposed portions 107 constituting the cross of the T. This element is secured in place by locating remote ends of the portions 107 in the vents and the stem 105 and its continuation 106 in the tubular means 99 so as to insure the inflow of metal will be thoroughly subjected to conditioning by the deoxidizing means both in the tubular means and chamber. The continuation 106 due to its slotted character serves to expedite melting thereof and conditioning of the metal. The free ends of the portions 107 of the element are preferably bevelled or pointed to some extent as shown in FIGS. 2 and 5 for disposition in side openings or vents 96 formed by the notches in the head portions so that some metal may flow outwardly through the vents to provide laterally extending arcuate portions 108 of a sample as depicted in FIG. 22 of said parent application, which will be described subsequently with respect to the device exemplified in FIGS. 2, 3 and 4.

The trigger assembly generally designated 104 is unique and preferably includes a generally U-shaped metal member 109 and a disc-like handle 110. The member has a leg 111 located between one of the portions 98 of the head sections and the tubular means 99 and a leg portion 112 between the portion 98 and the sleeve 102, a bridge portion 113 engaging an end of the portion 98, an offset inner end portion 114 extending into the chamber 95 and an outeroffset end 115 to which is connected the handle 110 or a tag. This trigger assembly affords a setup whereby after a sample has been obtained, the handle or tag can be pulled in the appropriate direction or directions whereby to assist in separating the sleeve 102 from the half sections and tubular means. It should be noted that means, such as cement or a washer 116 of pasteboard is preferably secured in the outer end of the sleeve and about the tubular means to provide a seal therebetween. It should also be noted that the side opening 92 above referred to, has a diameter to facilitate entry of the sleeve 102 of the device and that the opening 93 is larger than the opening 92 and accommodates the head or larger extremity of the device. It should be further noted that the device may be rotated about its axis relative to the connector to any position desired by an operator to facilitate entry of the tubular means into the molten metal. The tubular means 99 may be secured in place in the tubular formation formed by the channel portions 98 by the cement or as alluded to above.

Figure 2:
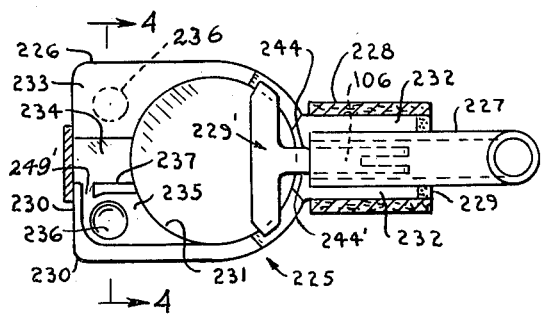
FIG. 2 is a longitudinal section taken substantially on line 2—2 of FIG. 3 of a modified device.
Figure 3:
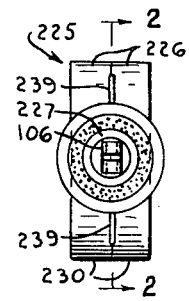
FIG. 3 is one end view of the device of FIG. 2.

FIGS. 2, 4 and 3 disclose a modified device generally designated 225 whereby a sample or portions may be obtained as shown in FIGS. 22, 23 and 24 of said parent application. The device 225 is substantially the same as the device 90 except that it includes half sections generally designated 226 which embody different and unique structural advantages. The device does include a tubular means 227, sleeve 228, washer or cement 229 and the deoxidizing element 229' like 103.

As to the half sections 226, each comprises a generally rectangular head portion 230 provided with a round recess 231, channel portions 232 (one shown) and a solid outer end portion 233 provided with an axially extending rectangular slot 234, a relatively shallow recess 235 which is provided with a substantially semispherical secondary chamber or pocket 236, a longitudinally extending rib 237 constituting a side wall of the slot 234. When the sections are correctly assembled, the recesses 231 define: a primary chamber for receiving molten metal from the tubular means 227, the side notches, openings or vents 239 for the portions of the deoxidizing element 229', the axial slots 234 an opening which receives a portion of an appendage 240, as shown in FIG. 22, the shallow recesses 235 on the opposite sides of the longitudinal axis of the device respectively provide relatively broad passages through which metal may flow into the opening formed by the axial notches 234. Otherwise expressed, metal may flow from the primary chamber into the secondary chambers 236 and vents 239 so that when the metal solidifies a sample or portions will be obtained as shown in FIGS. 22, 23 and 24 of said parent application. An appendage 240, like the appendage 31, is preferably disposed in the axial opening for imbedment in metal and clip means is also employed for detachably holding head portions of the sections together. The size of the secondary chambers 236 are preferably predetermined so that, for example, portions obtained will each weigh one gram. However, it is to be understood that these secondary chambers may be in different sizes and shapes.

More particularly, the sample or portions illustrated in FIGS. 22, 23 and 24 in said parent application, include a cylindrical stem portion 241 formed in the tubular means 227, a round head portion 242 of substantially uniform thickness which may correspond to the cross-dimension of the stem portion and an intermediate restricted portion 243 formed in a passage 244 of the sections. The material defining the passage constitutes an abutment 244'. Attached to the head 242 are circumferentially spaced relatively thin outwardly extending radial portions 108 formed in the side openings or vents 239, a pair of parallel relatively thin portions 246 of uniform thickness which are located on opposite sides of and in parallel relation to the longitudinal axis of the stem. The portion 246 are formed in the recesses 235 and extend in a direction opposite to that of the stem and the outer extremity of each of the portions 246 includes hemispherical portions 247 formed in the secondary chambers 236, each of which is intended to weigh, for example, one gram. It will be noted an axially extending portion 248 is formed in the opening formed by the slots 234 and that the portion 248 is joined to the outer extremities of the parallel portions 246 by portions 249 formed in passages 249'. It should also be noted that the head portion, parallel portions, axial portion and transverse portions define openings 250.

If found desirable, a deoxidizing element 251, as illustrated in FIG. 21 of said parent application, may be utilized in lieu of the element 103; for disposition in the tubular means 227. The element 251 is preferably resiliently flexible and in the form of a strip of aluminum which is rolled generally into a generally cylindrical shape and is provided with an internal portion 252. The outside diameter of the element is preferably slightly larger than the inside diameter of the tubular means 227 so the element when manually inserted into the tubular means will be automatically held in position. The element 251 is preferably adapted for disposition in the tubular means 227 and against the abutments 244' in lieu of utilizing the element 103.

FIG. 25 of said parent application, depicts a setup whereby a die comprising apertured members 253 and 254 may be used to obtain the sample portions 247. More specifically, in this respect the sample shown in FIG. 22 is so located that one of the portions 247 is received in an aperture of the lower die member and so that a portion 246 is clamped between the members to permit a punch 255 to sever the portion 247 from portion 246 for analysis. Obviously, any of the other portions such as 241, 242, 243 of the sample may be utilized for analysis.

Figure 7:
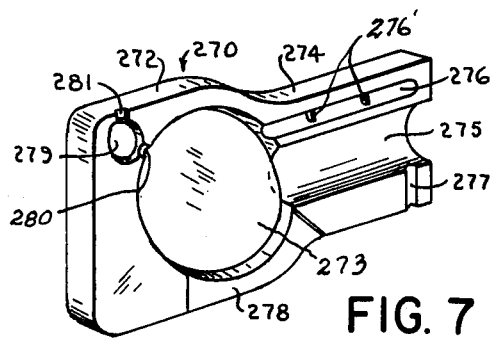
FIG. 7 is a perspective view of one of a pair of half sections of a modified device.
Figure 8:
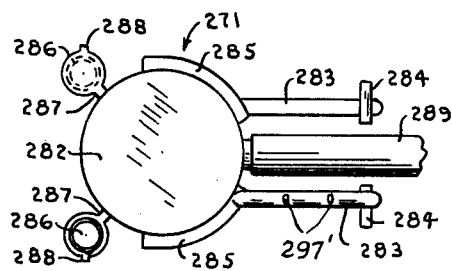
FIG. 8 is a face view of a sample obtained by using the device shown in FIG. 7.
Figure 9:
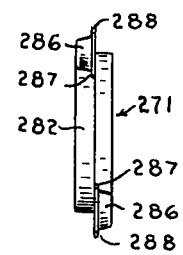
FIG. 9 is an end view of the sample shown in FIG. 8.
Figure 10:
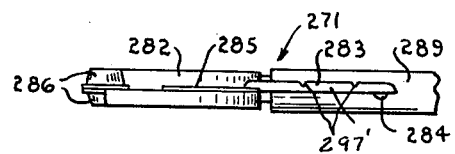
FIG. 10 is a side view of the sample shown in FIG. 8.

FIG. 7 is a perspective view of a modified form generally designated 270 of one of a pair of half sections which in combination with a tubular means, and a sleeve corresponding to those shown in FIG. 2, serve to obtain a sample generally designated 271 as exemplified in FIGS. 8, 9 and 10.

More particularly, each of the half sections 270 preferably comprises a head portion 272 provided with a large round recess 273 and a channel or extended portions 274 provided with a longitudinally extending semi-cylindrical center groove 275. The cross-dimension of the extended portion is preferably such that one side is provided with a longitudinally extending groove 276 disposed on one side of the center groove and the other side of an extended portion is provided with a transverse groove 277 constituting a side vent. The longitudinal grooves are preferably divided into three equal areas by a pair of projections or markers 276' for a purpose which will be described subsequently. The outer end of the groove 276 is closed and its inner end communicates with the recess 273. The head portion 272 of each section is also provided with a side notch 278 and with a relatively small recess 279 communicating with the round recess through a groove 280, and with the atmosphere through a groove 281.

When the sections and other components are correctly assembled to provide a device for receiving molten metal, the round recesses 273 will define a primary chamber for forming a sample having a head 282, the longitudinal grooves 276 will form a pair of longitudinal parallel portions 283, the transverse grooves 277 sample portions 284 joined to portions 283, the side notches 278 a pair of lateral arcuate portions 285 joined to the head portion 282 and portions 283, the small recesses 279 truncated solid portions 286, the grooves 280 and 281 the portions 287 and 288, and a tubular means will form a stem portion 289 which is straddled by the parallel portions 283.

Attention is directed to the fact that the portions 283, 284, 287 and 288 are substantially semi-circular in cross-section and this is due to the fact that each of the grooves in each half section forming such portions cooperate with a planar portion of the other half section. For example, the longitudinal groove 276 of half section 270 is covered by an abutting planar portion of an extended portion like 274 of a mating half section (not shown). Attention is also directed to the fact that except for the center groove 275 and round recesses 273 of the sections, all of the other grooves and smaller recesses define what may be termed a plurality of secondary chambers or cavities which receive molten metal for analysis in addition to the head and stem portion of the sample. The small truncated sample portions 286 obtained preferably have a weight of substantially one gram when severed from the head portion for analysis. It should be noted that the portions 286 are joined to the head portion by the portions 287 which are relatively thin whereby to facilitate severance of the portions and the portions 283 can also be readily severed from the head portion since they too are joined to the head by the portions 285 which are relatively thin in cross-section.

Attention is also directed to the important fact that the projections or markers 276', above referred to, serve to selectively divide and measure each of the longitudinal grooves 276 into three equal areas or zones as evidenced by the resulting notches or marking 297' of the samples shown in FIGS. 8 and 10. Each of the sample portions 297 thereby comprise three portions which may be readily separated at the notches to obtain for example, three separate samples, each weighing 1 gram for analysis.

It is to be understood that the half sections or receiving means can be fabricated from any material initially for the purpose, such as ceramic material, solid cast or forged metals such as copper, iron and steel, stamped from sheet metal stock. Sintered powdered metal is preferred because of certain unique characteristics it possesses. A properly designed powdered metal mold with adequate venting will form a fast chilled sample with a minimum of chemical segregation, optimum metalographic structure and precision dimensions for ease of preparation and analysis.

Elucidating further with respect to the use of the device in obtaining a sample, the sampling device is attached to the end of the lance or wand 4 so that the feed tube of the device is perpendicular to the axis of the pole. The individual taking the sample grasps the handle, faces the stream of molten metal, and holding the sample such that the feed tube of the device is near and parallel to the flow of the metal stream, twists the assembly so the open end of the feed tube is injected into the flow of the molten metal. The opening of the tube should be held at an angle to permit an unrestricted flow of the metal down the inside of the tube into the interior of the device. The open end of the tube is inserted just inside the outer surface of the steam to utilize the full volumetric capacity of the feed tube and minimize exposure of the incoming metal to the atmosphere.

As the sampling time using the invention so short, the sample size small and the mold enclosed, exposure to the atmosphere is greatly reduced, therefore reaction of the molten metal with oxygen is limited. Another important factor is the rapid transformation is accelerated by the mold design and the material employed. Rapid solidification minimizes chemical segregation and promotes a uniform structure.

It is theorized that when a molten metal sample is taken using powdered metal molds the sample is transformed quickly from the liquid to solid state by the combined action of the emissivity of the surface which allows the sintered iron mold to absorb the heat rapidly and the good conductivity of the iron allows the heat to transfer throughout the mass of the mold by conduction and convection. The good radiation characteristics of the outer surface allows for dissipation of the heat to the atmosphere. The quick chill effect of the mold design of the device coupled with its venting characteristics have permitted the design to incorporate the use of small extensions attached to the primary disc. These extensions are used primarily for the analysis of carbon and sulfur and their globular shape allows uniform cooling and solidification of the molten metal with a minimum of chemical segregation. Analysis of the elements from these samples may compare more favorably with analysis of drillings obtained from the primary disc and also with analysis obtained from product checks and possibly samples severed from glass enclosed pins which may cool differentially and have a tendency to segregate chemically.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. A device for obtaining a sample of liquid from a supply thereof, said device comprising a pair of elongated mating sections, each of said sections being provided with an enlarged portion provided with a recess and a smaller channel portion, means securing said enlarged portions together and means securing said channel portions together whereby said recesses and said channel portions respectively form a chamber and an elongated opening, said enlarged portions also having external side surfaces and cavities, inner passages connecting these cavities with said chamber for receiving fluid therefrom and outer passages venting said cavities at said surfaces, and a tube having an inner extremity secured in said opening and an outer extremity provided with an entrance for a liquid for flow into said chamber via said tube.

2. The device defined in claim 1, in which said first-mentioned means constitutes a component of said device and has leg portions straddling said enlarged portions and said means securing said channel portions comprises a sleeve which surrounds said channel portions and assists in holding said tube in said opening.

3. A device for obtaining sample of molten material from a supply thereof, said device comprising a pair of elongated half sections, each of said sections having an enlarged portion provided with a recess, a cavity and a small channel portion extending from said enlarged portion, means securing said sections together whereby said recesses, cavities and channel portions respectively form a primary chamber, secondary chambers and an elongated opening, inner passages connecting said primary and secondary chambers, said enlarged portions being formed to prevent axial flow of material from said primary chamber, outer passages venting said secondary chambers at the sides of said enlarged portions on opposite sides of the longitudinal axis of said device, and a tube having an inner extremity secured in said elongated opening and an outer extremity provided with means facilitating entry of a molten material into the tube for flow into said chambers.

4. A device for obtaining a sample of liquid from a supply thereof, said device comprising wall structure providing an enlargement having a closed end area and a forwardly extending extension respectively forming a primary chamber and an elongated opening communicating with said chamber, a tube having an inner extremity disposed in relation to said opening and an outer extremity provided with an entrance for entry into a liquid for its reception into the tube for flow into said chamber, and said enlargement having external side surfaces and a secondary chamber with an inner passage connecting said chambers and an outer passage for venting said secondary chamber at one of said side surfaces.

5. The device defined in claim 4, in which said extension is provided with a longitudinal chamber communicating with said primary chamber.

6. The device defined in claim 4, in which said extension is provided with a longitudinal chamber which communicates with said primary chamber and with indicia dividing said longitudinal chamber into different areas.

7. A device for obtaining a sample of molten material from a supply thereof, said device including a subassembly comprising a pair of elongated half sections, each of said sections comprising a head provided with a recess and a channel extension, means for engaging and securing said heads whereby the recesses and extensions respectively form a primary chamber and a tubular formation, tubular means having an inner extremity secured in said formation and an outer extremity provided with an entrance whereby such material may be caused to flow through said tubular means into said chamber, at least one of said extensions being provided with a secondary chamber for receiving material from said primary chamber, and at least one of said heads being provided with a side opening communicating with said primary chamber through which material may flow whereby solid sample portions formed in said chambers are joined together by an intermediate portion formed in said opening.

8. The device defined in claim 7, in which each of said heads is provided with a recess and a groove which respectively form additional chambers, located on a line transverse to the longitudinal axis of said device, and passages which establish communication with said primary chamber.

9. A subassembly of a device for obtaining a sample of liquid from a supply thereof, said subassembly comprising wall structure forming a head and an extension, said head being provided with a primary chamber, said extension being provided with a longitudinal entrance opening which is communicatively connected to said chamber, and said extension forming a pair of secondary chambers straddling said opening and communicating with said primary chamber, said chambers having internal surfaces for shaping a sample.

10. A subassembly for use as a component of a device for obtaining a sample of molten material from a supply thereof, said subassembly comprising wall structure forming an enlargement provided with internal surfaces forming a primary chamber and a reduced tubular formation having an entrance for entry into such material, said enlargement having an outer end area provided with internal surfaces forming a secondary chamber and a passage and said formation having surfaces forming a third chamber communicating with said primary chamber, the arrangement being such whereby molten material entering said entrance will flow through said passage into said secondary chamber and third chamber via said primary chamber for eventual solidification against the internal surfaces of said chambers to provide a sample having a large portion, a smaller portion, an elongated portion, intermediate restricted portions which join said smaller and elongated portion with said large portion within the confines of said enlargement and formation, and said outer area being solid opposite said entrance to prevent axial outflow of material from said primary chamber.

11. A structure for use as a means of a device for obtaining a sample of molten material from a supply thereof, said structure comprising walls forming an enlargement provided with a side vent and internal surfaces forming a primary chamber and a tubular formation having a longitudinally extending entrance, said formation being provided with internal surfaces forming a longitudinal secondary chamber extending alongside said entrance communicating with said primary chamber and vent whereby molten material entering said entrance will flow successively into said primary and secondary chambers for eventual solidification against the internal surfaces thereof whereby to form a sample substantially within the confines of said chambers which has a large portion and a smaller portion of a predetermined size extending from said large portion.

12. A structure for use as a means of a device for obtaining a sample of molten material from a supply thereof, said structure comprising walls forming an enlargement provided with internal surfaces forming a plurality of communicatively connected chambers and a tubular formation having a longitudinal entrance communicatively connected to all chambers for receiving material for flow into said chambers and against said surfaces for solidification therein, and said formation being provided with a pair of longitudinal chambers straddling said entrance and communicating with said connected chambers for receiving said material.

13. A device for obtaining a sample of liquid from a supply thereof, said device including a subassembly comprising a pair of half sections, each of said sections comprising a head provided with a recess and a channel extension provided with a side longitudinal groove, means for securing said sections whereby the recesses, extensions and side grooves respectively form a primary chamber, a tubular formation provided with a longitudinal entrance and longitudinal secondary chambers straddling said entrance whereby liquid may be caused to flow through said entrance into said primary and secondary chambers to engage their internal surfaces.

14. The device defined in claim 13, in which each extension is provided with means for dividing the longitudinal groove into predetermined areas.

15. The device defined in claim 13, in which the heads of said sections are provided with additional recesses which respectively form additional chambers, and passages establish communication between said primary chamber and said additional chambers.

16. A device for obtaining a sample of molten material, said device comprising wall structure forming an enlargement provided with a primary chamber and a tubular formation forming a longitudinal entrance through which such a material may be caused to flow into said chamber, said enlargement also being provided with a secondary chamber, a side opening and a restricted passage, and said formation being provided with a longitudinal chamber at one side of said entrance whereby material may be caused to flow into said chambers whereby the material upon solidification will form a sample comprising a relatively large portion, and a pair of smaller portions of different shapes are joined to said large portion by intermediate restricted portions.

17. A subassembly comprising wall structure for use in a device for obtaining a sample of molten metal, said wall structure forming a body having a head and provided with a tubular entrance, said head being provided with a primary chamber for receiving molten metal through said entrance, said head having outer corner areas and external side surfaces, a secondary chamber provided in at least one of said corner areas, a restricted passage in said one area communicatively connecting said secondary chamber to said primary chamber for receiving molten metal therefrom, and a passage intersecting one of said side surfaces and communicating with said secondary chamber for venting the latter.

18. A subassembly comprising wall structure for use in a device for obtaining a sample of molten metal, said wall structure forming a body having a head provided with a primary chamber, tubular means extending from said head for receiving molten metal for flow into said chamber, said head having relatively thick generally squared outer areas having external surfaces, a secondary chamber provided in at least one of said areas, an inner restricted passage connecting said secondary chamber with said primary chamber for receiving molten metal from said primary chamber, and an outer passage intersecting at least one of said surfaces and connected to said secondary chamber for venting the latter.

19. A sample made from molten metal comprising a head portion, a stem portion joined to and extending from said head portion, and a pair of portions respectively joined to said head portion by intermediate restricted portions in straddling relation to said stem portion.

20. A molten metal sample comprising a head portion, a stem portion joined to and extending from said head portion, and an elongated portion joined to said head portion by an intermediate restricted portion and extending alongside of and substantially parallel to said stem portion.

21. The sample defined in claim 20, including a portion integral with an extending from said elongated portion.

22. The sample defined in claim 20, in which said elongated portion is joined to the head portion in a manner whereby to facilitate severence of said elongated portion therefrom.

23. A sample made from molten metal comprising a head portion, a stem portion extending from said head portion, and a pair of portions joined to said head portion by relatively thin intermediate curved portions and disposed in a straddling relation to said stem portion.

24. The sample defined in claim 23, including a pair of additional portions joined to said head portion at locations remote from said straddling portions on opposite sides of the longitudinal axis of said sample.

25. A sample made from molten metal comprising a head portion joined to and extending from said head portion, and a lateral portion joined to said head portion at a location remote from said stem portion by an intermediate curved restricted portion whereby to facilitate severence of said lateral portion from said head portion.

26. A sample made from molten metal comprising a head portion, by a relatively thin intermediate restricted portion whereby to facilitate severence of said extending portion, and said extending portion is provided with spaced means whereby to facilitate severence thereof into segments.

27. A sample made from molten metal comprising a head portion, a pair of lateral portions joined to said head portion by intermediate restricted portions and extending therefrom in different directions, and a pair of additional portions joined to said head portion and extending therefrom in directions generally opposite to said first pair.

* * * * *